US009101577B2

(12) United States Patent
Bujalska-Zadrozny et al.

(10) Patent No.: US 9,101,577 B2
(45) Date of Patent: Aug. 11, 2015

(54) ANALGESIC PHARMACEUTICAL COMPOSITION FOR ORAL ADMINISTRATION

(75) Inventors: Magdalena Bujalska-Zadrozny, Warsaw (PL); Marek Naruszewicz, Zalesie Górne (PL)

(73) Assignee: Warszawski Uniwersytet Medyczny, Warszawa (PL)

(*) Notice: Subject to any disclaimer, the term of this patent is extended or adjusted under 35 U.S.C. 154(b) by 0 days.

(21) Appl. No.: 14/122,712

(22) PCT Filed: May 31, 2012

(86) PCT No.: PCT/PL2012/050016
§ 371 (c)(1),
(2), (4) Date: Jan. 13, 2014

(87) PCT Pub. No.: WO2012/165985
PCT Pub. Date: Dec. 6, 2012

(65) Prior Publication Data
US 2014/0127302 A1 May 8, 2014

(30) Foreign Application Priority Data

May 31, 2011 (PL) .......................... 395069

(51) Int. Cl.
*A61K 31/485* (2006.01)
*A61K 33/06* (2006.01)
*A61K 33/14* (2006.01)
*A61K 45/06* (2006.01)
*A61K 31/137* (2006.01)
*A61K 31/135* (2006.01)
*A61K 31/19* (2006.01)
*A61K 31/194* (2006.01)
*A61K 9/16* (2006.01)
*A61K 31/197* (2006.01)

(52) U.S. Cl.
CPC ............... *A61K 33/14* (2013.01); *A61K 31/135* (2013.01); *A61K 31/137* (2013.01); *A61K 31/19* (2013.01); *A61K 31/194* (2013.01); *A61K 31/485* (2013.01); *A61K 33/06* (2013.01); *A61K 45/06* (2013.01); *A61K 9/16* (2013.01); *A61K 9/1611* (2013.01); *A61K 31/197* (2013.01); *Y10S 514/951* (2013.01)

(58) Field of Classification Search
CPC .................................................. A61K 31/485
See application file for complete search history.

(56) References Cited

U.S. PATENT DOCUMENTS

| | | | |
|---|---|---|---|
| 2002/0051794 A1* | 5/2002 | Soni et al. | 424/278.1 |
| 2003/0008011 A1* | 1/2003 | Mershon | 424/487 |
| 2004/0022872 A1* | 2/2004 | Sofue et al. | 424/692 |
| 2004/0048870 A1* | 3/2004 | Amir et al. | 514/250 |
| 2004/0259899 A1* | 12/2004 | Sanghvi et al. | 514/282 |
| 2007/0259033 A1* | 11/2007 | Cruz | 424/452 |
| 2008/0220064 A1* | 9/2008 | Ramesh et al. | 424/485 |

OTHER PUBLICATIONS

Allen et al., "Magnesium stearate", Aug. 9, 2005, pp. 430-433.*

(Continued)

*Primary Examiner* — Isaac Shomer
(74) *Attorney, Agent, or Firm* — Kilyk & Bowersox, P.L.L.C.

(57) ABSTRACT

The disclosed analgesic pharmaceutical composition for oral administration is characterized in that it contains an opioid and a pharmaceutically admissible magnesium (II) compound, possibly along with one or more pharmaceutically admissible ancillary substances.

10 Claims, 15 Drawing Sheets

(56) References Cited

OTHER PUBLICATIONS

S Begon, G Pickering, A Eschalier, C Dubray. Allen et al., "Magnesium Increases Morphine Analgesic Effect in Different Experimental Models of Pain." Anesthesiology, vol. 96, 2002, pp. 627-632.*

SM Berge, LD Bighley, DC Monkhouse. "Pharmaceutical Salts." Journal of Pharmaceutical Sciences, vol. 66 No. 1, Jan. 1977, pp. 1-19.*

International Search Report issued in corresponding International Patent Application No. PCT/PL2012/050016 dated Aug. 23, 2012 (4 pages).

Endo Pharmaceuticals, Inc., "Morphine Sulfate (morphine sulfate) Tablet," Apr. 2006, pp. 1-14.

Ulugol et al., "Combined systemic administration of morphine and magnesium sulfate attenuates pain-related behavior in mononeuropathic rats," Brain Research, vol. 943, 2002, pp. 101-104.

Assi, "The Influence of Divalent Cations on the Analgesic Effect of Opioid and Non-Opioid Drugs," Pharmacological Research, vol. 43, No. 6, 2001, pp. 521-529.

Begon et al., "Magnesium Increases Morphine Analgesic Effect in Different Experimental Models of Pain," Anesthesiology, vol. 96, No. 3, Mar. 2002, pp. 627-632.

Bujalska et al., "Magnesium ions and opioid agonists in vincristine-induced neuropathy," Pharmacological Reports, vol. 61, 2009, pp. 1096-1104.

* cited by examiner

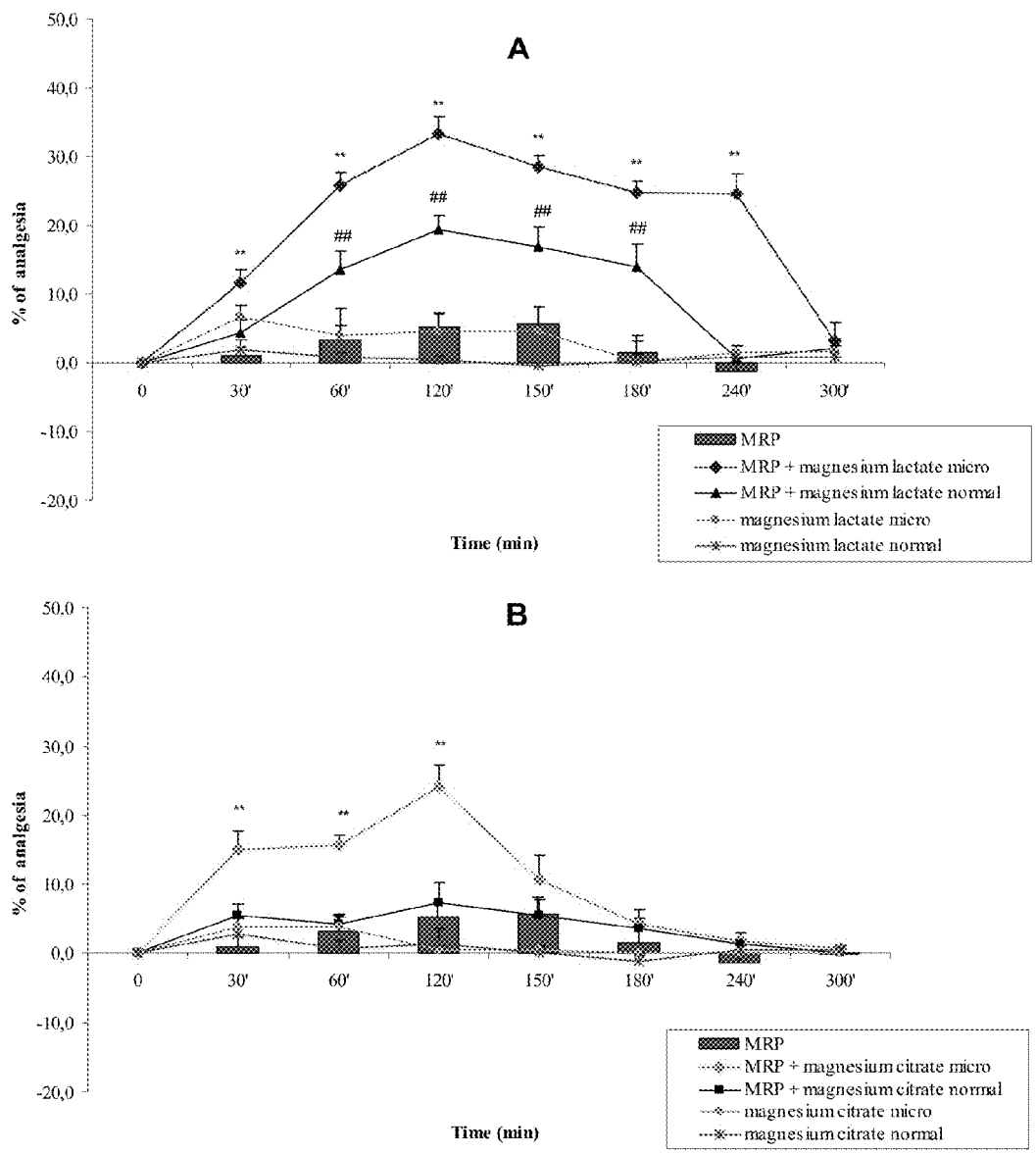

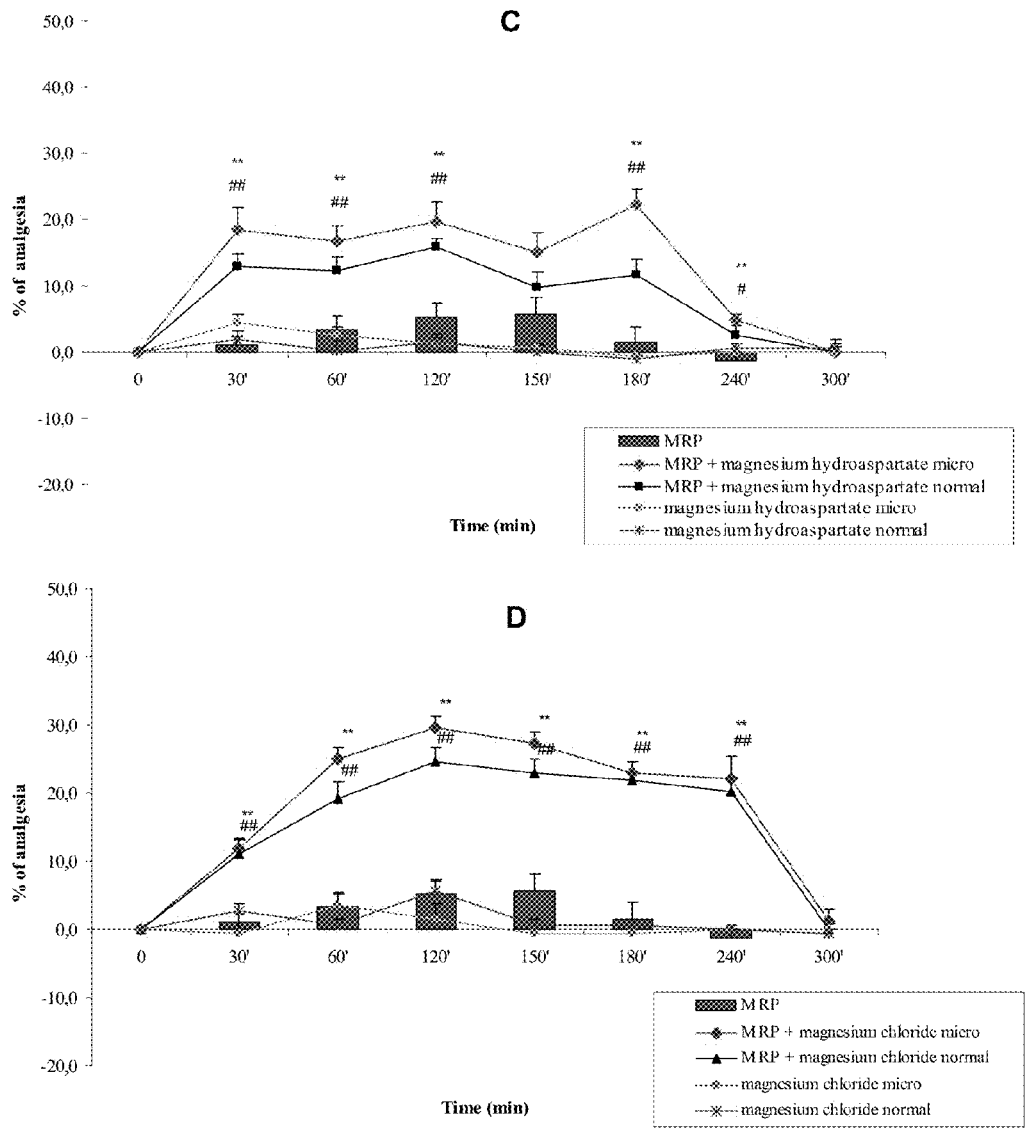
Values are means ± S.E.M.
\*\* $p < 0.01$ morphine vs. morphine + micronized magnesium compound
$p < 0.01$ # $p < 0.05$ morphine vs. morphine + normal magnesium compound Values are means ± S.E.M.

** $p < 0,01$ * $p < 0,05$ morphine (MRF) vs. morphine + micronized magnesium compound

$p < 0,01$ # $p < 0,05$ morphine vs. morphine + normal magnesium compound

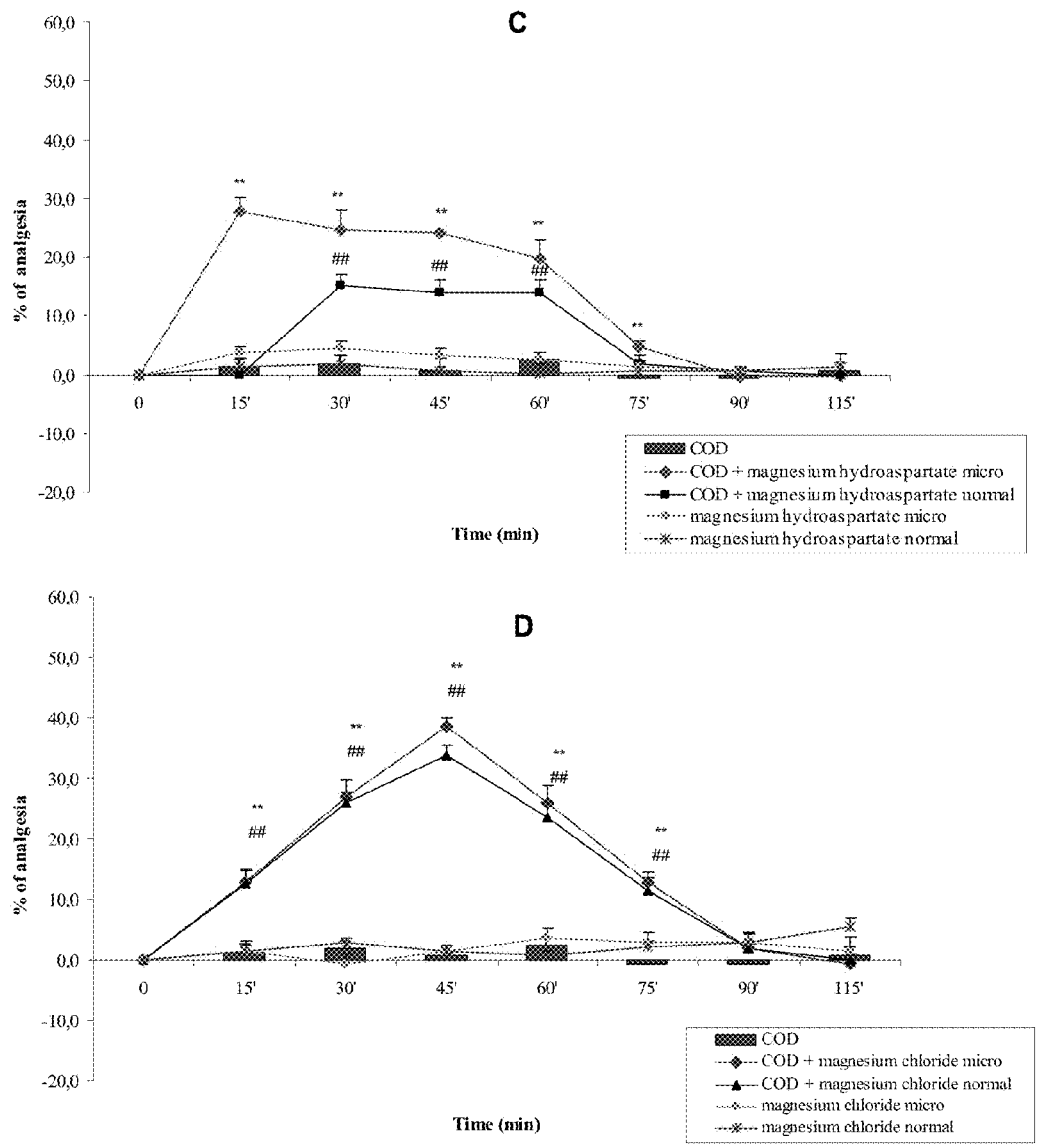
Values are means ± S.E.M.
\*\* p < 0,01  \* p < 0,05  codeine  vs.  codeine + micronized magnesium compound
## p < 0,01  # p < 0,05  codeine  vs.  codeine + normal magnesium compound Values are means ± S.E.M.

** p < 0,01   codeine   vs.   codeine + micronized magnesium compound ## p < 0,01   # p < 0,05   codeine   vs.   codeine + normal magnesium compound

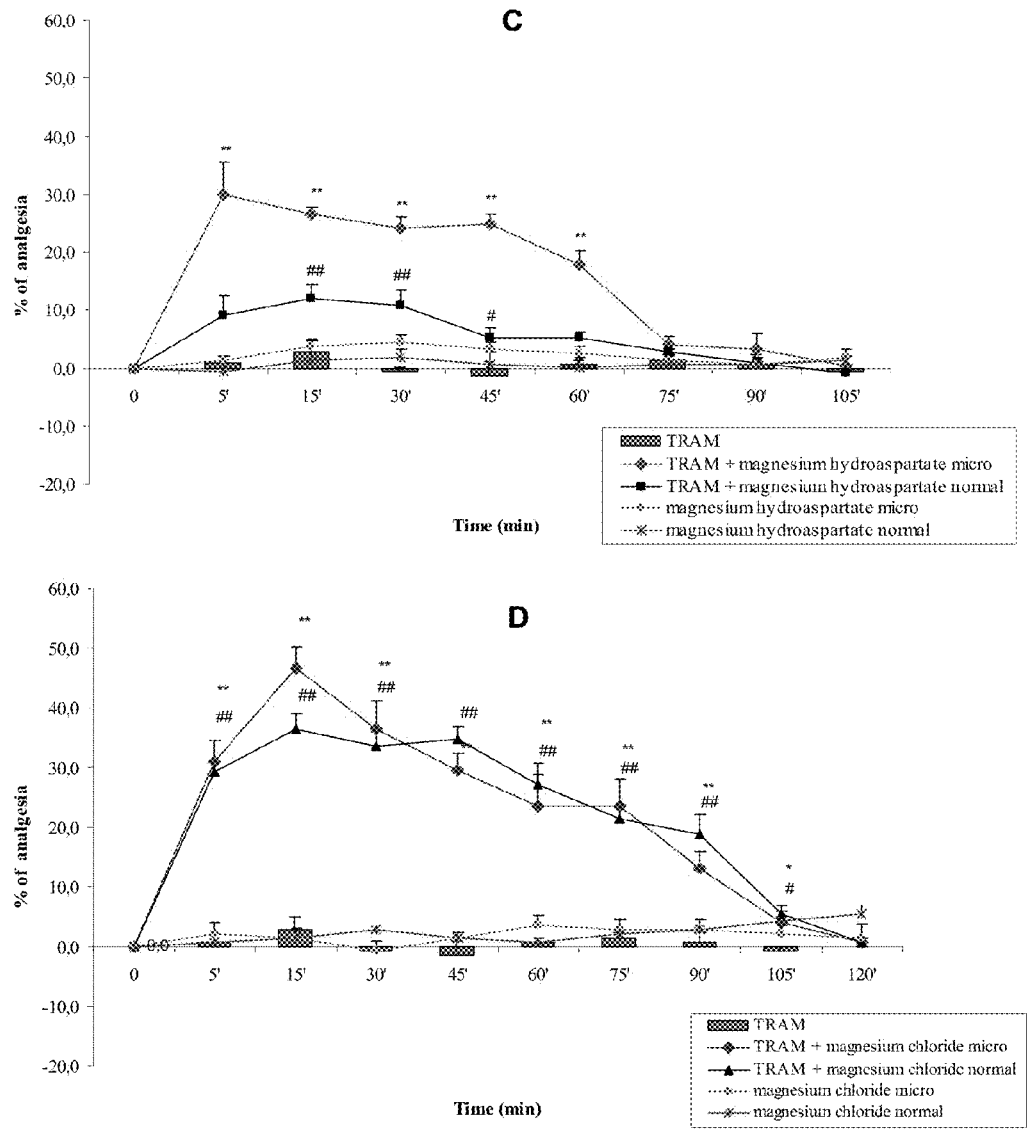

Values are means ± S.E.M.

** $p < 0{,}01$  * $p < 0{,}05$  tramadole  vs.  tramadole + micronized magnesium compound

$p < 0{,}01$  # $p < 0{,}05$  tramadole  vs.  tramadole + normal magnesium compound

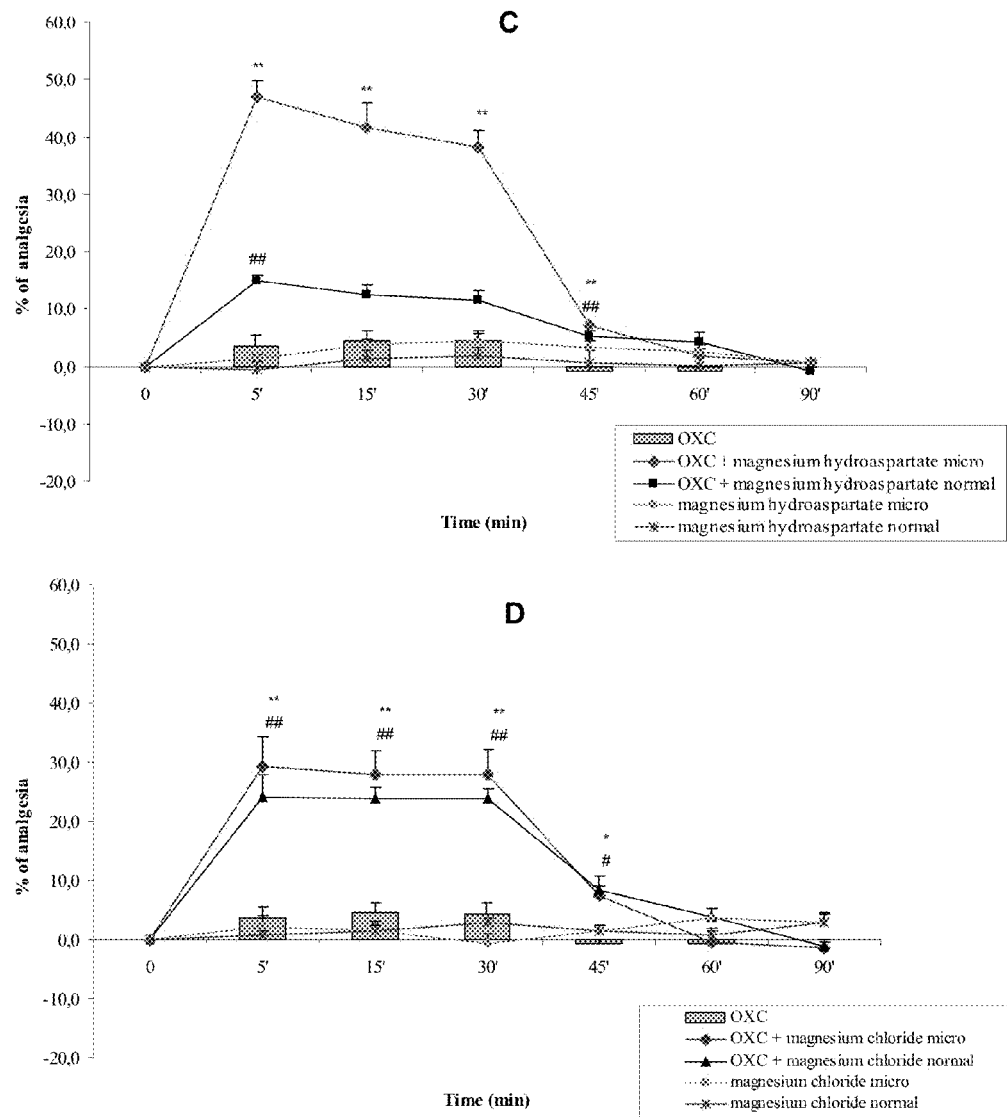
Values are means ± S.E.M.
** p < 0,01 oxycodone vs. oxycodone + micronized magnesium compound
## p < 0,01 oxycodone vs. oxycodone + normal magnesium compound Values are means ± S.E.M.

** p < 0,01 oxycodone vs. oxycodone + micronized magnesium compound ## p < 0,01  # p < 0,05  oxycodone vs. oxycodone + normal magnesium compound

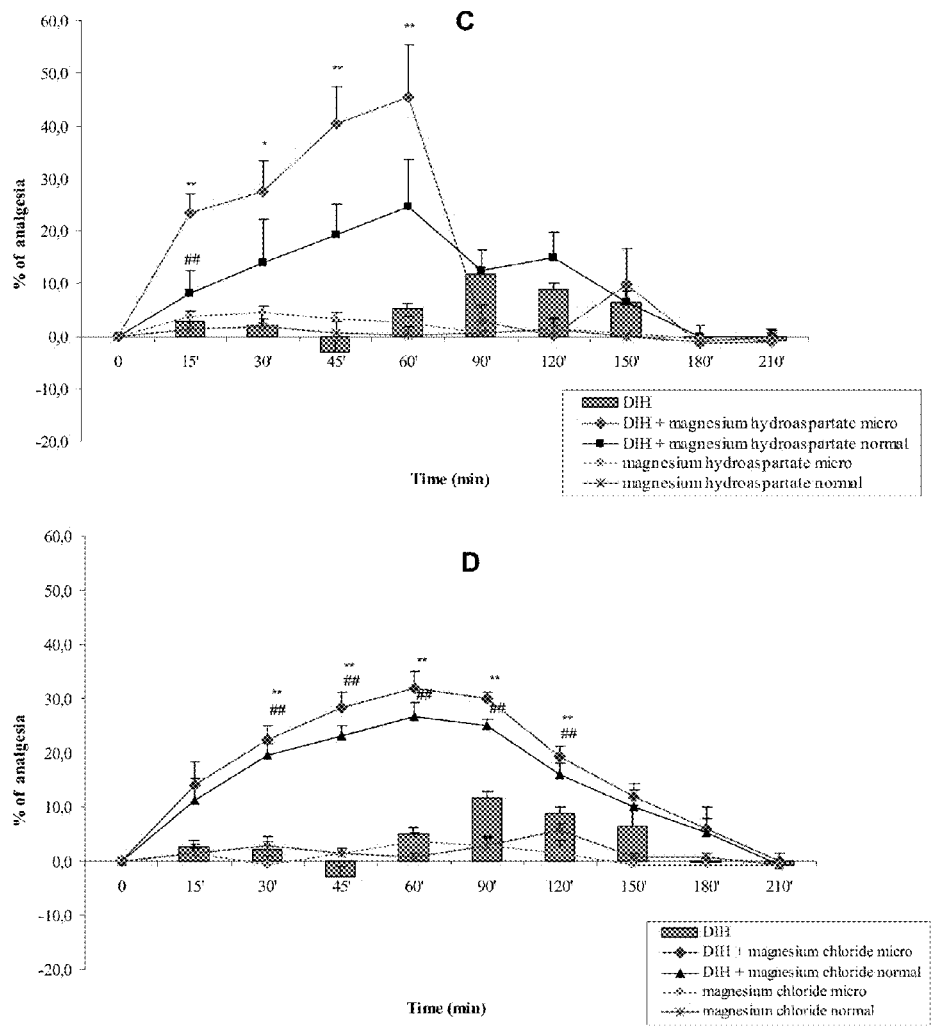
Values are means ± S.E.M.
\*\* p < 0,01  \* p < 0,05 dihydrocodeine vs. dihydrocodeine + micronized magnesium compound
## p < 0,01  dihydrocodeine  vs.  dihydrocodeine + normal magnesium compound Values are means ± S.E.M.

** p < 0,01 dihydrocodeine vs. dihydrocodeine + micronized magnesium compound
## p < 0,01 dihydrocodeine vs. dihydrocodeine + normal magnesium compound

ANALGESIC PHARMACEUTICAL COMPOSITION FOR ORAL ADMINISTRATION

This application is a National Stage Application of PCT/PL2012/050016, filed May 31, 2012.

The presented invention relates to an analgesic pharmaceutical composition for oral administration.

The treatment of severe pain, particularly pain in final stages of neoplasm diseases, still remain an unsatisfactorily resolved problem in modern medicine. The algorithm of pain treatment is based on the rule that the stronger pain, the more effective and more strongly acting analgesic is needed. This schematic is also known by the common name of the analgesic ladder, on which individual rungs are occupied by nonsteroidal analgesics, then weak opioids, and finally potent opioid analgesics. This schematic also encompasses the use of ancillary drugs (adjuvants) which may enhance opioid activity (the so-called co-analgesics). In the absence of other, equally effective analgesic drugs, opioids are increasingly often used in treatment. At present, they are used not only in alleviating cancer or post-operative pain, but are also used for relief of other pain for instance in rheumatoid arthritis.

Unfortunately, the results of analgesic treatment have been unsatisfactory for years. The insurmountable barrier is a limit in analgesic opioid effectiveness connected with, for instance, development of tolerance, the resistance of neuropathic pain to analgesic opioids, or the so-called "paradoxical pain" following opioid use. Another problem consists of the undesirable effects of opioids, which also limit their utility. These are, amongst others: chronic constipation, dizziness, disturbances of central nervous system, such as consciousness disorders, cognitive impairment or respiratory depression (particularly in the case of an overdose).

In clinical practice, in order to reduce opioid doses, and thereby to avoid the risk of deleterious side effects, attempts have been made to introduce co-analgesics, which enhance the analgesic activity of opioid like drugs that block N-methyl-D-aspartate (NMDA) receptors, or drugs that stimulate the GABA-ergic system. However, these compounds are often accompanied by undesirable effects, which limits their use.

It is well-known that magnesium (II) is a physiological antagonist of NMDA receptors, the activation of which is responsible for the development of various types of pain. Likewise, is commonly known the laxative activity of orally administered magnesium salts.

The aim of this invention is to create a pharmaceutical composition of analgesic drugs containing an opioid, which makes it possible to conduct a more effective analgesic therapy. It is particularly desirable to limit the daily dose of opioid and, consequently, to limit the risk of undesirable effects of opioid use. This should particularly delay the development of tolerance to analgesic opioid activity as weli as the development of physical addiction. It is particularly desirable to obtain a novel composition in the form of a tablet for oral administration, which would increase the availability of such a drug and enable its use at home.

Unexpectedly, such stated goals have been achieved by the present invention. The subject of the present invention is an analgesic composition for oral administration, characterised by that it contains an opioid and a pharmaceutically admissible magnesium (II) compound, possibly with one or more pharmaceutically admissible ancillary substances.

Preferably, a composition according to the present invention is characterised in that the opioid is selected from a group containing phenantrene derivatives of opium: morphine, codeine, dihydrocodeine, oxycodone. According to invention, using an atypical opioid (tramadol) and opioids from other groups is also acceptable.

Examples of ancillary substances necessary for the manufacturing of an orally administered drug form, such as tablets or capsules, include fillers (e.g. sugars such as lactose, glucose or saccharose, alcohol sugar derivatives, such as mannitol, sorbitol, or xylitol, starches such as wheat, corn or potato starch), lubricants such as talcum, magnesium stearate, calcium stearate, colloidal silica or stearic acid, or binders such as polyvinylpyrrolidone or cellulose derivatives (carboxymethylcellulose, hydroxypropylcellulose, hydroxypropylmethylcellulose, methylcellulose) or gelatin. The tablets may be, for ease of use, coated with an appropriate film-form agent, e.g. hydroxypropylmethylcellulose, hydroxypropylcellulose, polivinyl alcohol or ethylcellulose, which may optionally be supplemented with ancillary substances, i.e. a softener such as glycerol, propylene glycol, diethyl phthalene or glycerol triacetate; a filler such as saccharose, sorbitol, xylitol, glucose or lactose; and a dye such as titanium dioxide, iron oxides, etc.

Equally preferable, a composition according to the present invention is characterised in that a magnesium (II) compound is a pharmaceutically admissible salt of magnesium, preferably selected from a group containing: magnesium lactate, magnesium chloride, magnesium hydroaspartate and magnesium citrate. According to the present invention, using any other pharmaceutically admissible compound of magnesium (II) is acceptable, regardless of its hydration level or crystalline form (polimorphic/amorphic). According to the present invention, it is also possible to use pharmaceutically admissible magnesium (II) coordination complexes.

According to a particular version of the present invention, the magnesium (II) compound is in the form of micronized particles of D90<200 μm, preferably D90<50 μm.

Without going into detail, in light of the results shown below, it seems that the rate of magnesium ion ($Mg^{2+}$) absorption in vivo is dependent not only on the solubility of the relevant magnesium compounds (e.g. pharmaceutically admissible salts), but also on the degree of micronization of these substances. When magnesium is used in the form of particles of lesser dimentions, it probably results in faster magnesium absorption in vivo from an oral composition with an opioid, and it is manifested by an enhanced analgesic synergy between opioid and magnesium ions. In terms of the method of obtaining a micronized magnesium (II) compound, a number of methods are available which make it possible to obtain particles D90<200 μm in diameter. The simplest method is micronization. However, one should not limit oneself to this method as a specialist is capable of proposing a series of other methods which make it possible to obtain particles of a desirable size or their obvious functional equivalents characterized by a developed active surface. Such methods include: production of a molecular dispersion, spraying a solution onto neutral carrier grains, or other methods largely consisting of spraying or dripping a magnesium compound and evaporation of the solvent.

The next subject of the present invention is the use of a combination of an opioid and a magnesium (II) compound in the production of analgesic preparation for oral administration, which consists of an opioid and a pharmaceutically admissible magnesium (II) compound, possibly with one or more pharmaceutically admissible ancillary substances.

The preferable characteristics of a preparation produced according to the present invention have been show above.

A particular version of the present invention is an analgesic composition for oral administration containing an opioid and a salt of magnesium (II), especially in micronized form. Particularly preferable is the use of an opioid in long-acting form, i.e. morphine sulphate.

According to the present invention, it unexpectedly turned out that orally administered magnesium enhances the analgesic effect of a concomitantly administered opioid, in particular morphine, codeine, tramadol, oxycodone and dihydrocodeine or their pharmaceutically admissible salts. Unexpectedly, a particularly beneficial synergy of analgesic activity was observed when the magnesium salts administered orally with the opioid were in micronized form (D90<50 µm).

In the studies on rats described below, it was shown in particular that the micronized form of magnesium salts were significantly more effective in enhancing the analgesic activity of orally administered opioids than traditional form of magnesium salts.

Analgesia was also observed following the concomitant administration of small doses of micronized magnesium salts and small doses of the investigated opioids, which showed non-analgesic activity when given separately. Furthermore, it was observed that a composition according to the present invention decreases the incidences of opioid-induced constipation.

The magnesium (II) salt dose used in the examples described below (15 mg magnesium ions/kg body mass of the rat) is a very small dose.

For instance, the magnesium lactate (2×500 mg) dose used in clinical trials is also a small dose, and is indicated as a supplementary dose. Supplementation makes use of 5-10 mg/kg/day of magnesium ions. Therefore, for a patient weighing 70 kg this is 350-700 mg/day. The proposed daily magnesium salt dose (51-102 mg of magnesium ions/person; 25.5-51 mg of magnesium ions in one tablets) is also a very small dose.

An oral composition being the version of the present invention, particularly in the form of tablets containing a pharmaceutically admissible opioid form with protracted effects and a pharmaceutically admissible magnesium (II) compound will make it possible to use the unexpected analgesic synergy between opioids and magnesium in practice.

Because salts of magnesium have a laxative effect, the oral administration of a magnesium (II) compound with an opioid additionally alleviates one of the most common undesirable effects of opioids i.e, troublesome constipation. The risk of this complication is reduced in two ways by a composition according to the present invention: firstly, by decreasing the size of the effective dose and secondly, due to the laxative effect (desirable in this case) of the magnesium (II) compound contained in the composition.

In a particular version of the present invention, a preparation composed of an opioid with a magnesium (II) compound also allows simplification of the dosage schedule (a patient takes two substances in one tablet instead of two tablets). Delivery of the composition in a single tablet makes it possible to use this combination not only in inpatient care but at home as well.

According to an alternative version of the present invention, an oral analgesic preparation is possible in two separate forms, one containing an opioid and a micronized magnesium (II) compound or an opioid and a non-micronized magnesium (II) compound.

In order to better demonstrate the concept of the present invention, this description is supplemented with the following figures:

FIG. 1 represents the influence of magnesium salts (lactate—A, citrate—B and hydroaspartate—C, chloride—D) in micronized form (micro) and a normal form at a dose of 15 mg magnesium ions/kg body mass (per os; [p.o.]) on the analgesic activity of morphine (MRP) at a dose of 15 mg/kg body mass (p.o.);

Figure 3:
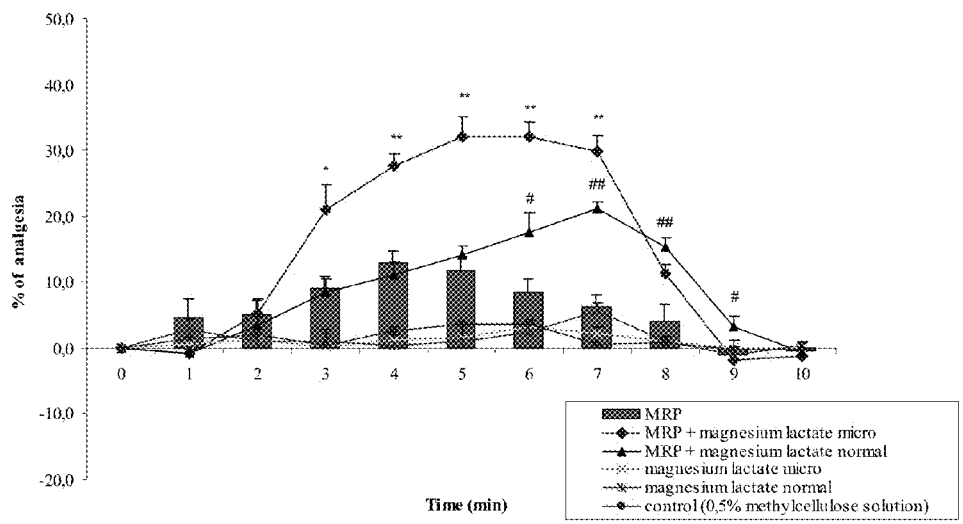
Figure 4:
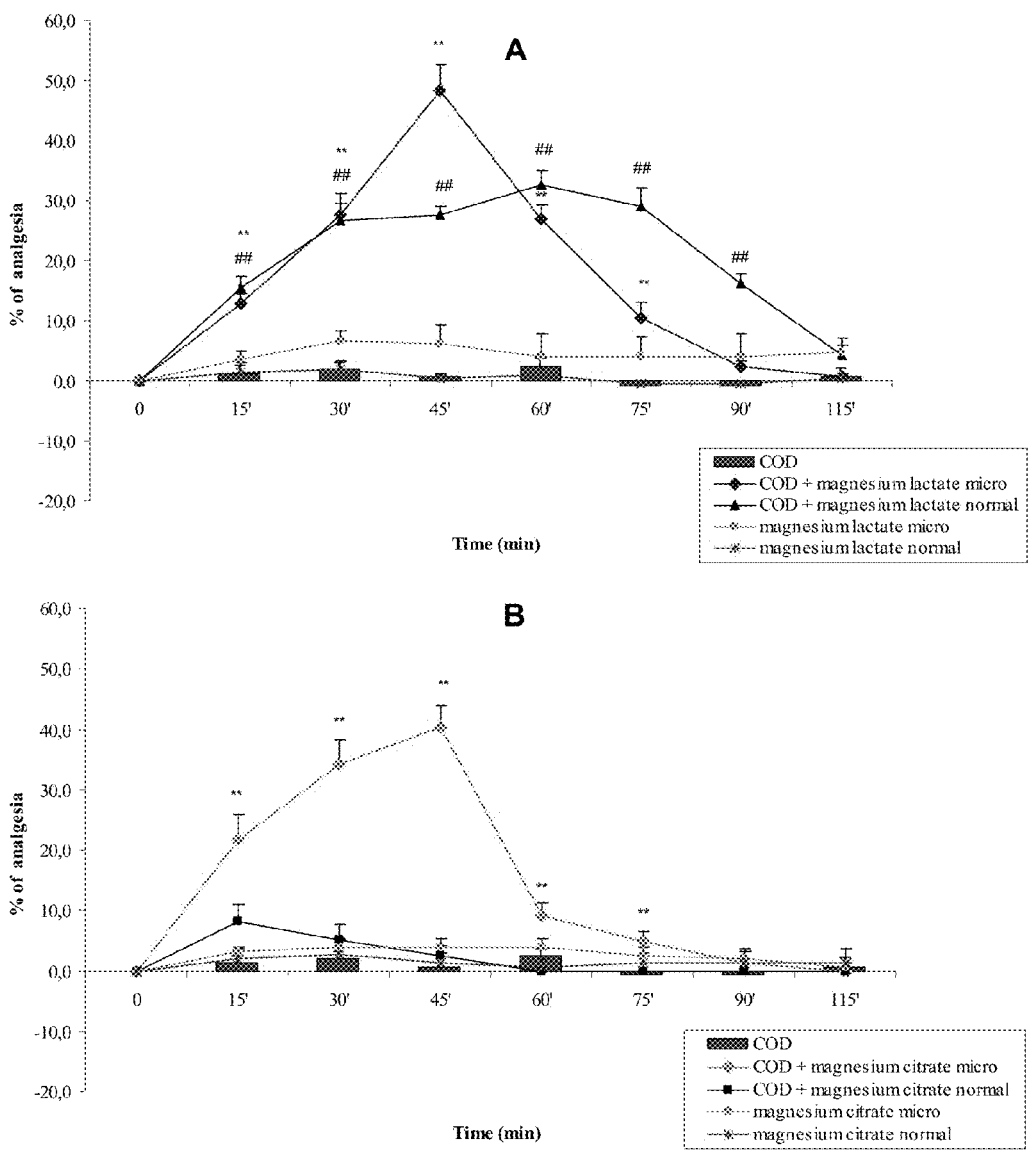
Figure 5:
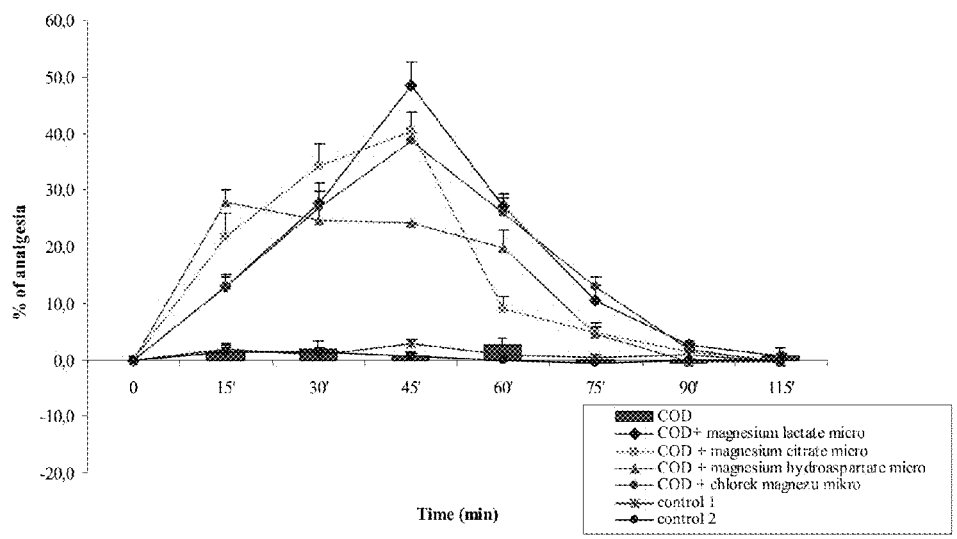
Figure 6:
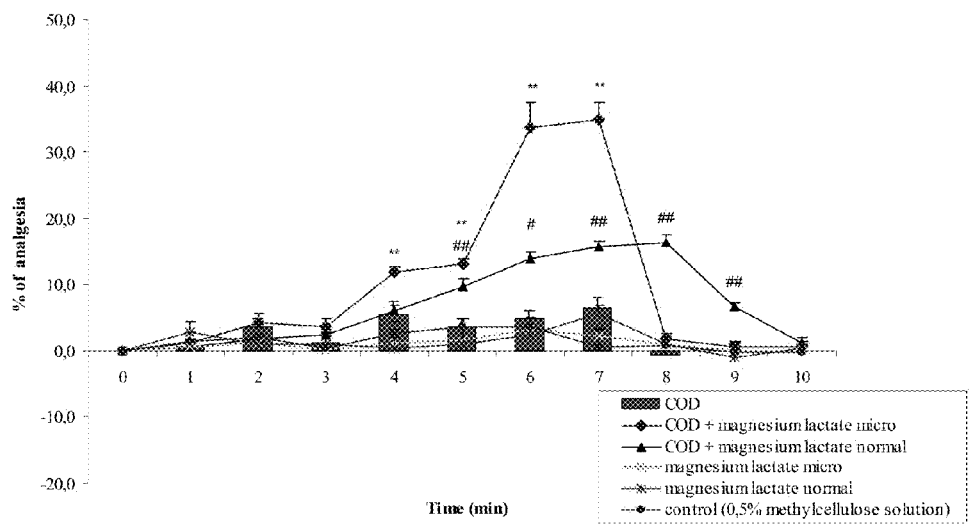
Figure 7:
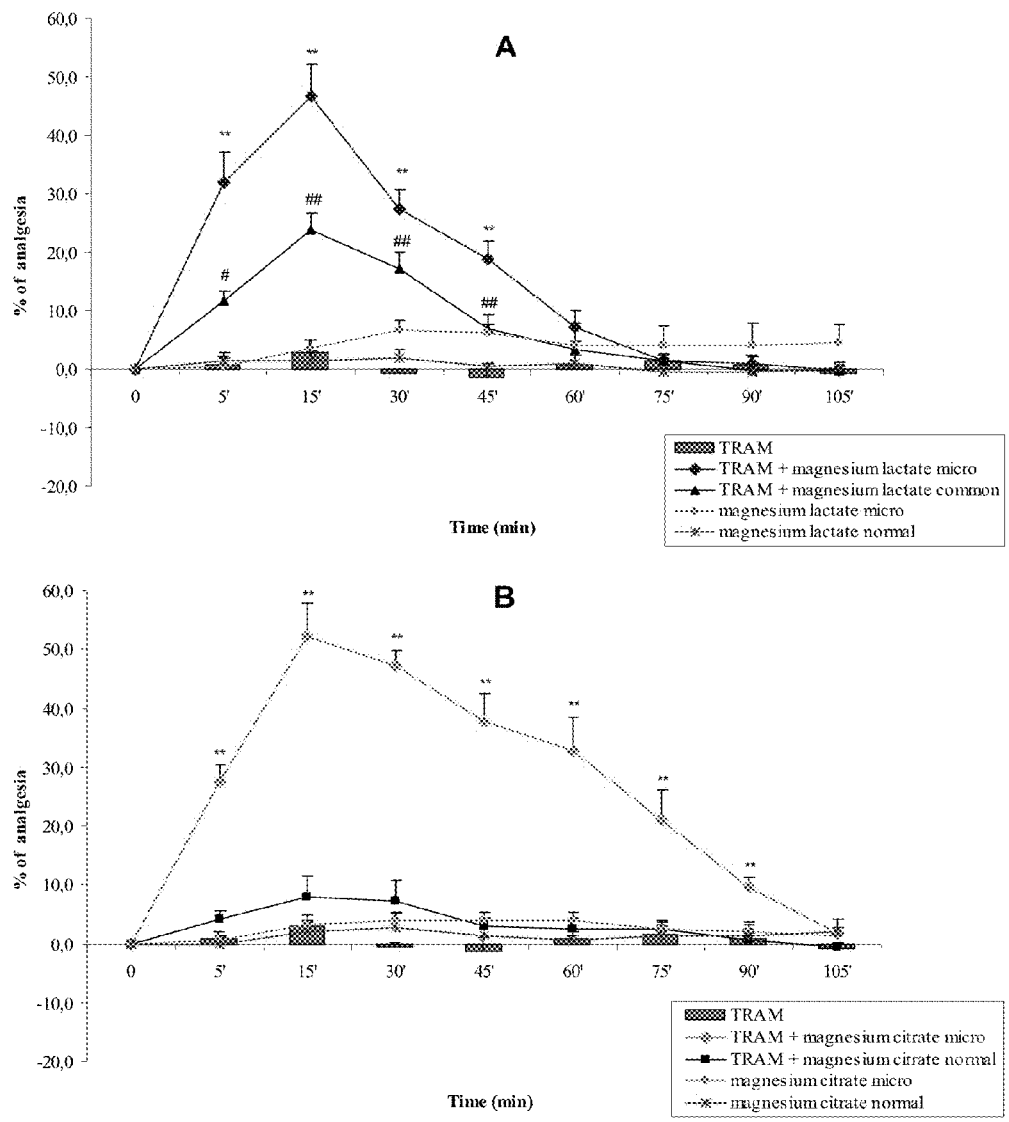
Figure 8:
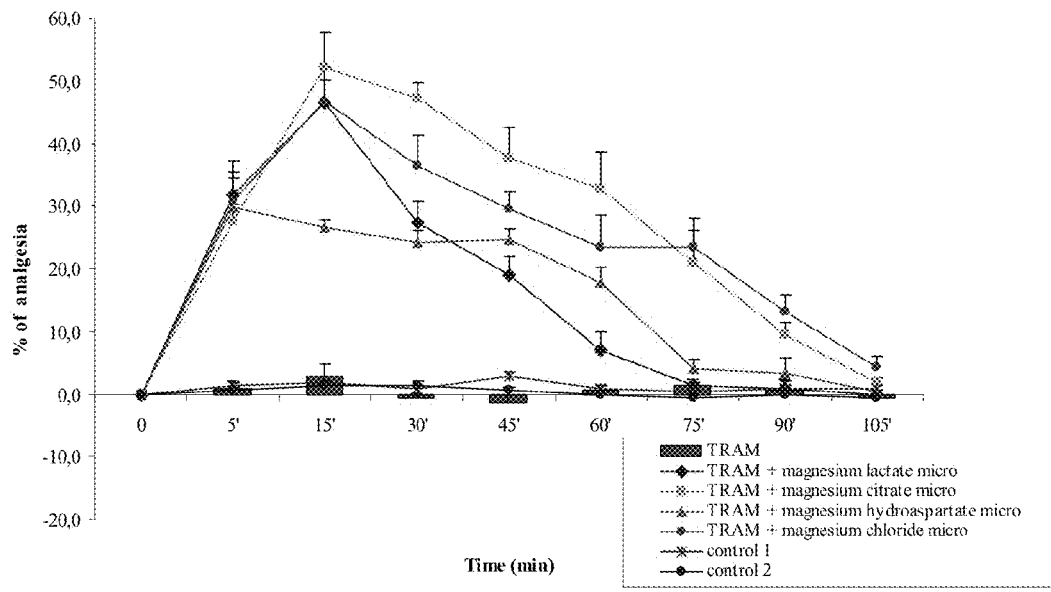
Figure 9:
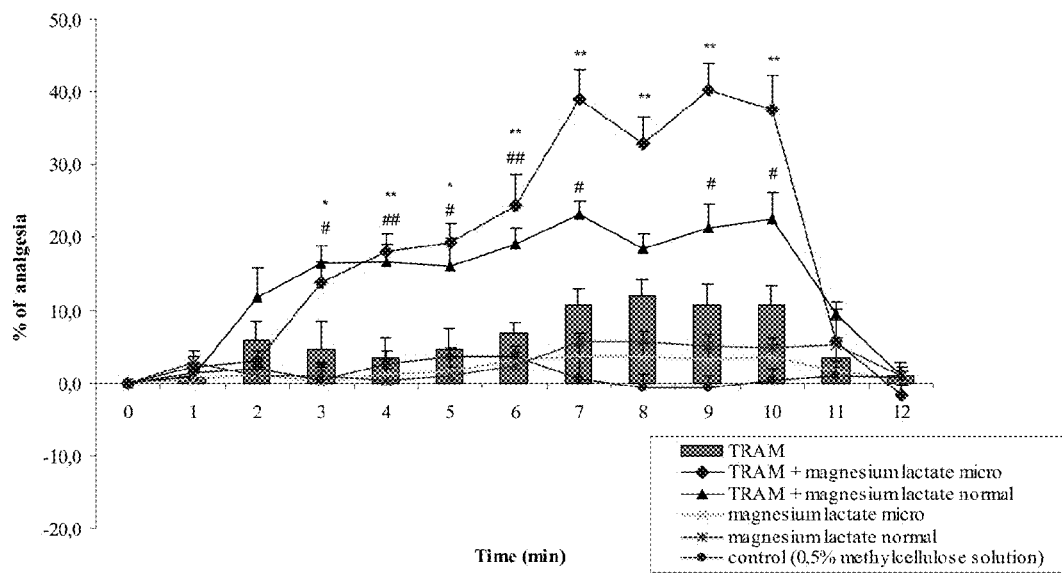
Figure 10:
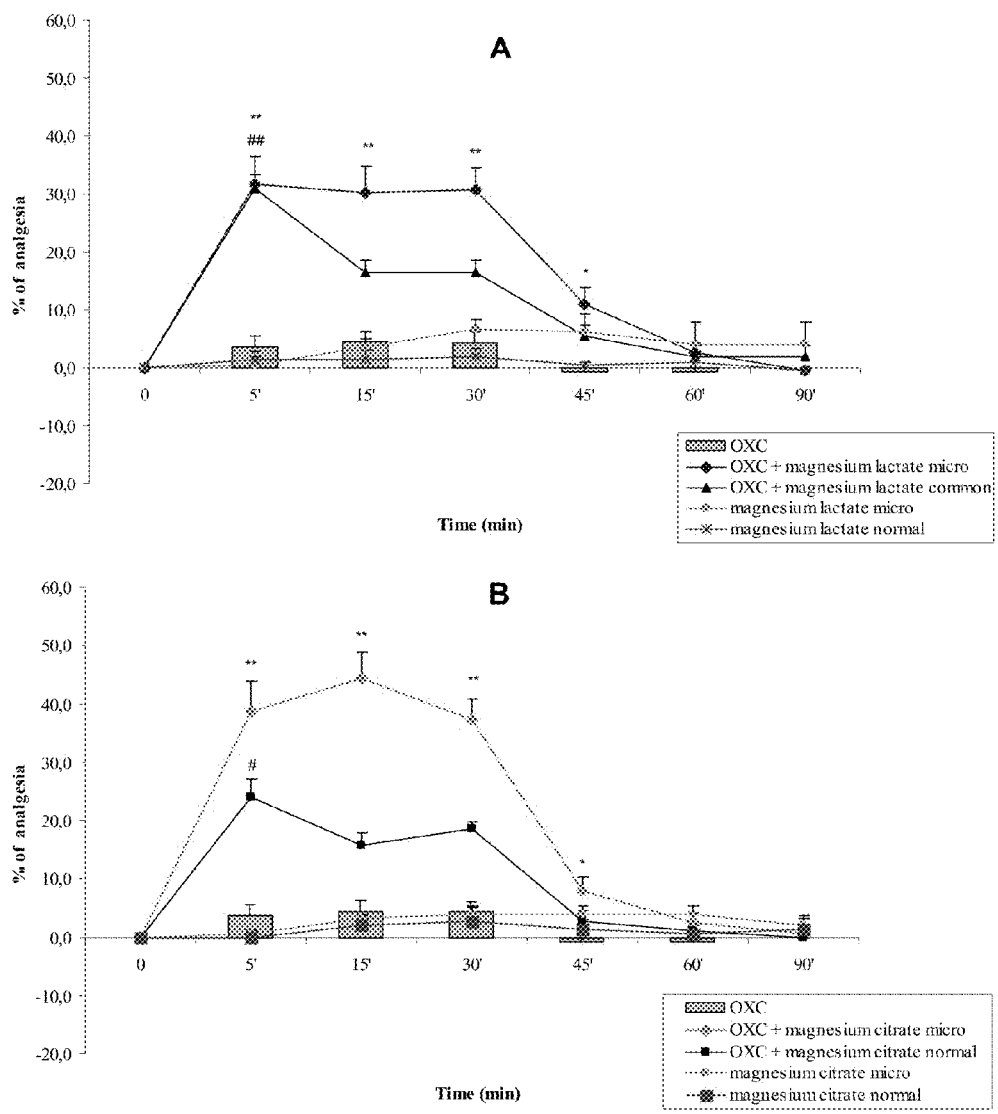
Figure 11:
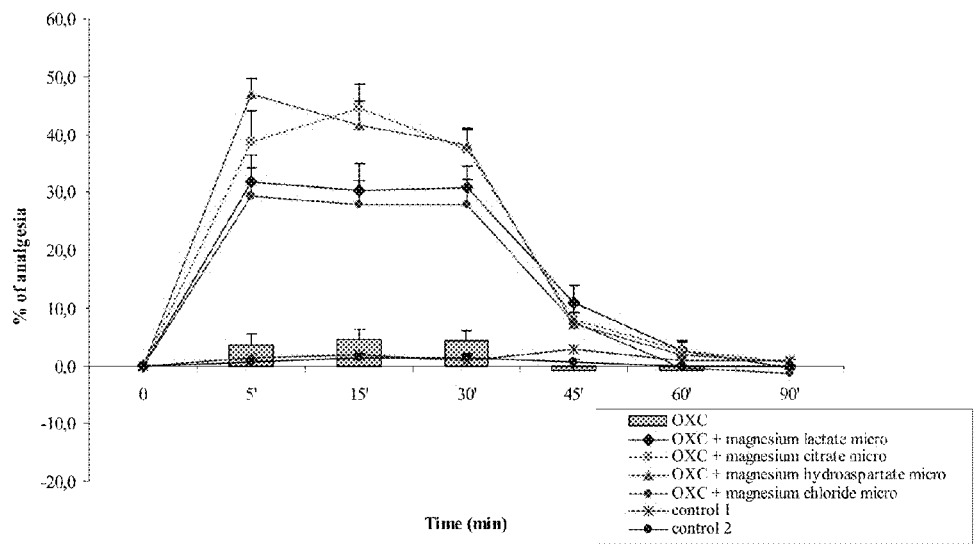
Figure 12:
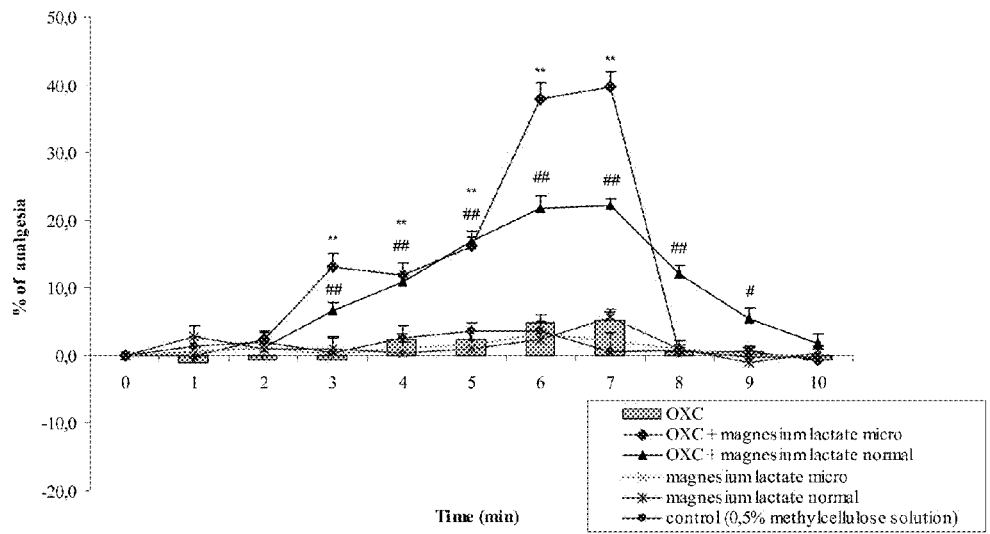
Figure 13:
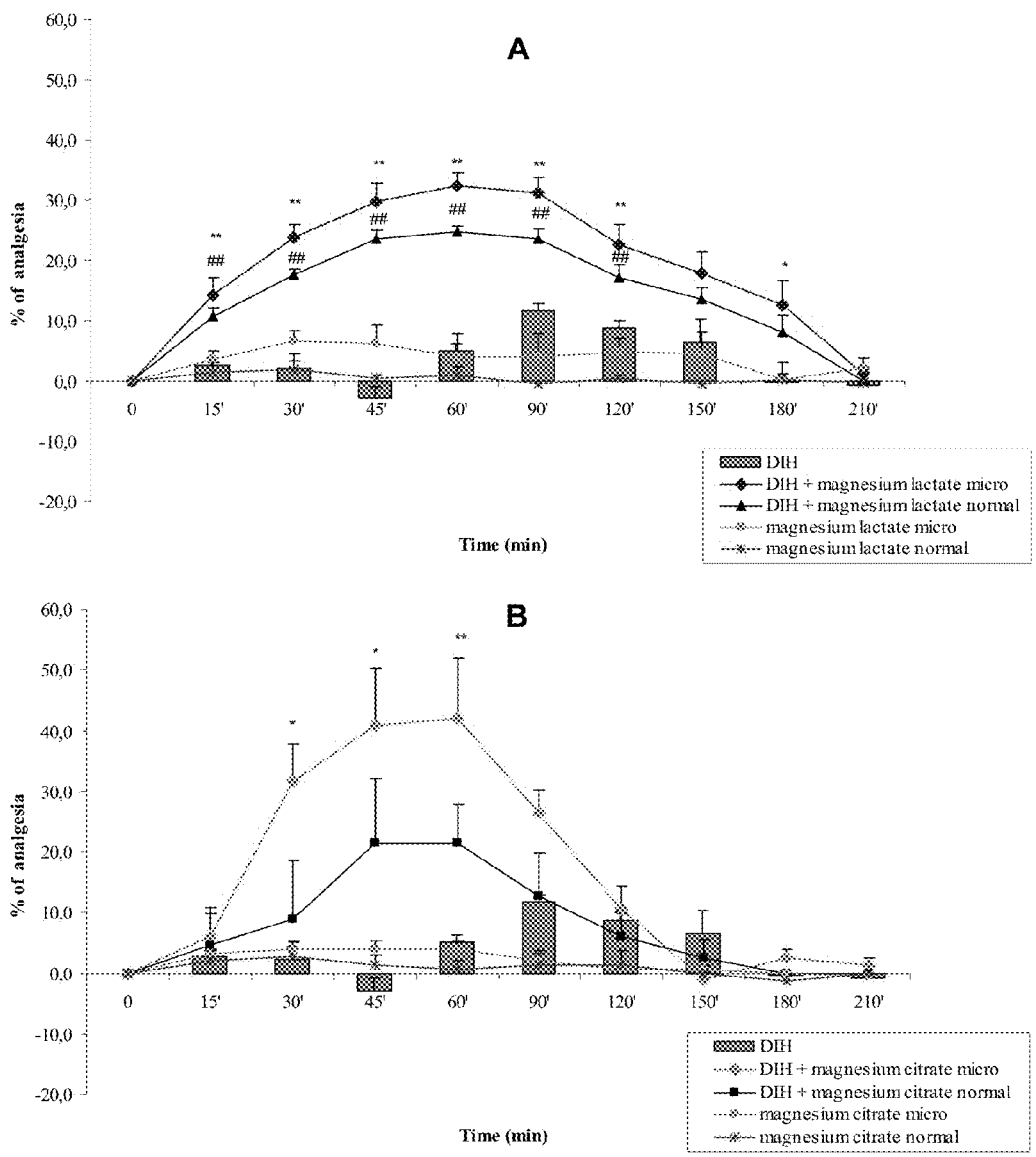
Figure 14:
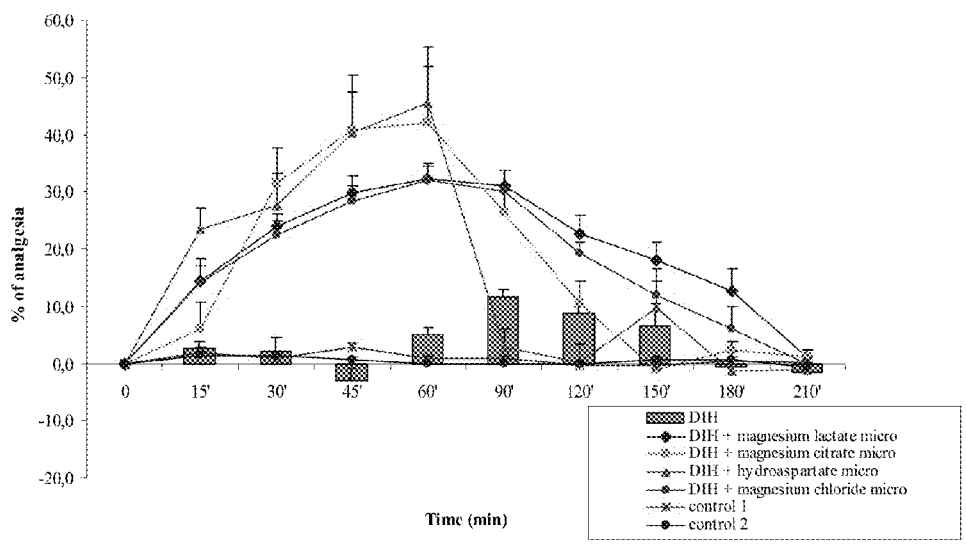
Figure 15:
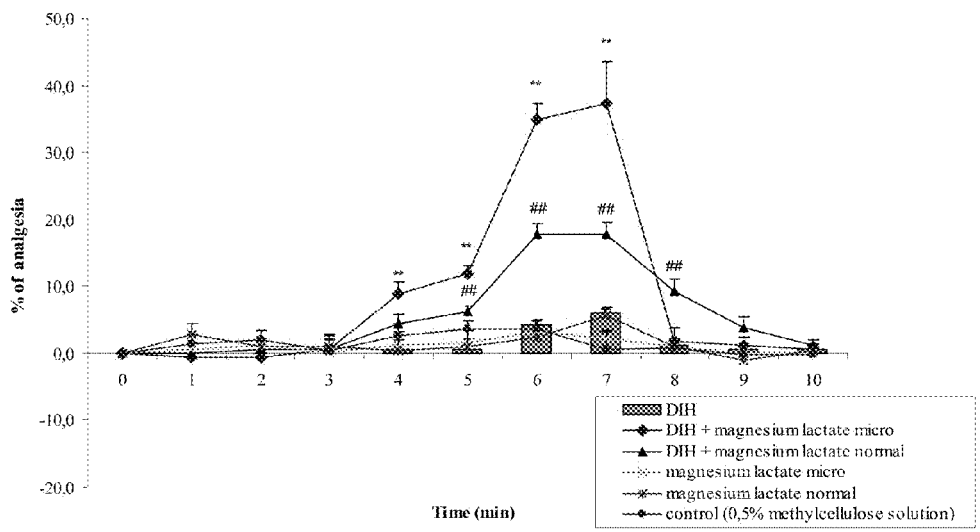

FIG. 3 represents the effect of long-term, 7-day administration of magnesium lactate in micronized form (micro) or normal form (15 or 30 mg magnesium ions/kg body mass [p.o.], respectively) on the analgesic activity of morphine (MRP, 15 mg/kg body mass, p.o.). Day 0—measurement of the initial pain threshold and the first day of administration of the tested compounds, days 1-7—measurement of the prolonged activity of the tested drugs, days 8-10—measurement following the cessation of administration;

FIG. 4 represents the influence of magnesium salts (lactate—A, citrate—B, hydroaspartate—C, chloride—D) in micronized form (micro) and normal form at a dose of 15 mg magnesium ions/kg body mass (p.o.) on the analgesic activity of codeine (COD) at a dose of 175 mg/kg body mass (p.o.);

FIG. 5 represents the effect of magnesium salts at a dose of 15 mg magnesium ions/kg body mass on the codeine analgesia (COD, 175 mg/kg body mass, p.o.). Wherein in the combined graph: control 1—0.5% methylcellulose solution, control 2—distilled water;

FIG. 6 represents the effect of long-term 7-day administration of magnesium lactate in micronized form (micro) or normal form (15 or 30 mg magnesium ions/kg body mass [p.o.], respectively) on the analgesic activity of codeine (COD, 175 mg/kg body mass, p.o.). Day 0—measurement of the initial pain threshold and the first day of administration of tested compound, days 1-7—measurement of the prolonged activity of the tested drugs, days 8-10—measurement following the cessation of administration;

FIG. 7 represents the effect of magnesium salts (lactate—A, citrate—B, hydroaspartate—C, chloride—D) in micronized form (micro) and normal form at a dose of 15 mg magnesium ions/kg body mass (p.o.) on the analgesic activity of tramadol (TRAM) at a dose of 125 mg/kg body mass (p.o.);

FIG. 8 represents the effect of magnesium salts at a dose of 15 mg magnesium ions/kg body mass (p.o.) on the tramadol analgesia (TRAM, 125 mg/kg body mass, p.o.). Wherein in the combined graph: control 1—0.5% methylcellulose solution, control 2—distilled water;

FIG. 9 represents the effect of long-term 10-day administration of magnesium lactate in micronized (micro) form or normal form (15 or 30 mg magnesium ions/kg body mass [p.o], respectively) on the analgesic activity of tramadol (TRAM, 125 mg/kg body mass, p.o.). Day 0—measurement of the initial pain threshold and the first day of administration of tested compound, days 1-10—measurement of the prolonged activity of the tested drugs, days 11-12—measurement following the cessation of administration;

FIG. 10 represents the effect of magnesium salts (lactate—A, citrate—B, hydroaspartate—C, chloride—D) in micronized form (micro) and normal form at a dose of 15 mg magnesium ions/kg body mass (p.o.) on the analgesic activity of oxycodone (OXC) at a dose of 5 mg/kg body mass (p.o.);

FIG. 11 represents the effect of magnesium salts at a dose of 15 mg magnesium ions/kg body mass (p.o.) on the oxycodone (OXC) analgesia at a dose of 5 mg/kg body mass (p.o.). Wherein in the combined graph: control 1—0.5% methylcellulose solution, control 2—distilled water;

FIG. 12 represents the effect of long-term 7-day administration of magnesium lactate in micronized (micro) or normal form (15 or 30 mg of magnesium ions/kg body mass [p.o.], respectively) on the analgesic activity of oxycodone (OXC, 5 mg/kg body mass, p.o.). Day 0—measurement of the initial pain threshold and the first day of administration of tested compound, days 1-7—measurement of the prolonged activity of the tested drugs, days 8-10—measurement following the cessation of administration;

FIG. 13 represents the effect of magnesium salts (lactate—A, citrate—B, hydroaspartate—C and chloride—D) in micronized form (micro) and normal form at a dose of 15 mg magnesium ions/kg body mass (p.o.) on the analgesic activity of dihydrocodeine (DIH) at a dose of 50 mg/kg body mass (p.o.);

FIG. 14 represents the effect of magnesium salts at a dose of 15 mg magnesium ions/kg body mass (p.o.) on dihydrocodeine analgesia (DIH, 50 mg/kg body mass, p.o.). Wherein in the combined graph: control 1—0.5% methylcellulose solution, control 2—distilled water;

FIG. 15 represents the effect of long-term, 7-day administration of magnesium lactate in micronized (micro) form or normal form (15 or 30 mg of magnesium ions/kg body mass, [p.o.], respectively) on the analgesic activity of dihydrocodeine (DIH, 50 mg/kg body mass, p.o.). Day 0—measurement of the initial pain threshold and the first day of administration of tested compound, days 1-7—measurement of the prolonged activity of the tested drugs, days 8-10—measurement following the cessation of administration.

Furthermore, the description is supplemented with the following examples:

EXAMPLE 1

Preparation of Tablets Containing Morphine and Magnesium Lactate

Tablet cores with the following composition:

| | |
|---|---|
| magnesium lactate in micronized form with particles of D90 < 200 μm or D90 < 50 μm in size: | 250 mg |
| morphine sulphate | 30 mg |
| lactose monohydrate | 48.17 mg |
| corn starch | 14.40 mg |
| modified starch | 9.60 mg |
| polyvinylpyrrolidone 25.000 | 4.00 mg |
| magnesium stearate | 0.80 mg | have been prepared by producing a granulate via wet granulation. Next, the remaining ancillary substances were added. Such a mixture produced was used to compress tablets on a rotary tabletter. Next, the tablets were coated with a polymer film. The resulting tablets demonstrate excellent mechanical parameters.

EXAMPLE 2

Intensification of Analgesic Effect of Orally Administered Opioids by the Oral Administration of Magnesium Ions Experimental Part Materials
Animals The study was conducted according to the guidelines of the Ethical Committee for Experiments on Small Animals, Medical University of Warsaw. The aforementioned Committee approved the experiment protocols.

Male Wistar rats (250-300 g) were housed in a room maintained at a temperature of 20±2° C. under 12 h-12 h light-dark cycles. The animals had free access to food and water. Experimental groups consisted of six rats.

Drugs

Morphine at a dose of 15 mg/kg, codeine at a dose of 175 mg/kg, tramadol at a dose of 125 mg/kg and oxycodone at a dose of 5 mg/kg were dissolved in distilled water;

Dihydrocodeine at a dose of 50 mg/kg was suspended in 1% solution of methylcellulose;

Magnesium lactate (in micronized form)—at a dose of 15 mg magnesium ions/kg (150 mg of magnesium lactate/kg) was suspended in 0.5% solution of methylcellulose;

Magnesium lactate in normal (non-micronized) form—at doses of 15 or 30 mg magnesium ions/kg (150 or 300 mg of magnesium lactate/kg, respectively) was suspended in 0.5% solution of methylcellulose;

Magnesium citrate (in micronized and normal form)—at a dose of 15 mg magnesium ions/kg (112 mg of magnesium citrate/kg) was dissolved in distilled water;

Magnesium hydroaspartate (in micronized and normal form)—at a dose of 15 mg magnesium ions/kg (216 mg of magnesium hydroaspartate/kg) was suspended in 0.5% solution of methylcellulose;

Magnesium chloride (in micronized and normal form)—at a dose of 15 mg magnesium ions/kg (59.5 mg of magnesium chloride/kg) was dissolved in distilled water;

Control animals received a 0.5% solution of methylcellulose, a 1% solution of methylcellulose and distilled water, respectively, according to the same time schedule.

In the mentioned studies, doses of opioids and magnesium salts were selected experimentally, so that the separately administered investigated drugs did not reveal significant analgesic action. Magnesium salts and investigated opioids were administered concomitantly.

The micronized form of magnesium salts used in experiments contains particles of magnesium compounds of size D90<50 μm.

The normal magnesium salts form used in experiments contains particles of sizes commonly available in the market.

Methods

Acute activity of investigated drugs was measured in short time periods (from 5 to 300 min) after single administration.

Prolonged activity of the investigated drugs was measured the following day after initial administration, but before the next administration as well as after cessation of administration. Drugs were administered for seven consecutive days (administration of morphine, codeine, dihydrocodeine, oxycodone) or for ten days (administration of tramadol).

All drugs were administered per os (p.o.); literally—orally. However, in practice, drugs were administered intragastric via a gastric tube.

Measurement of the Nociceptive Threshold.

Changes in pain thresholds were determined using a mechanical stimuli—the modification of the classic paw withdrawal test described by Randall and Selitto [1957]. In order to produce mechanical stimulation, progressively increasing pressure was applied to the dorsal surface of the rat's paw using an analgesymeter. The instrument used increased the force on the paw at a rate of 32 grams per second. The nociceptive threshold was defined as force in grams, at which the rat attempted to withdraw its right hindpaw and values of pressure were recorded at this very moment. At least two observers controlled the response.

Nociceptive thresholds (average of two trials) measured for each animal before single administration of investigated drugs (measurement of acute activity) or in day 0 before the first administration (measurement of prolonged activity) constituted the baseline pain threshold—A. Next, measurements of the withdrawal threshold to mechanical stimuli were performed at 5, 15, 30, 60, 90, 120, 180, 240, 300 min after drug administration (measurements of acute activity) or every day before drug administration (measurements of prolonged activity)—B.

In all experimental sessions (i.e. every day, each drug investigated) values of thresholds obtained (B) were compared to baseline (A).

Changes in pain threshold were calculated as a percent of baseline value according to the following formula:

$$C = \left(\frac{B}{A} \cdot 100\%\right) - 100\%$$

C—% of analgesia; A—pressure (in g), baseline pain threshold; B—pressure (in g) in consecutive measurements.

Percents of analgesia values calculated as above for individual animals were subsequently used to calculate average values in particular experimental groups and for statistical analysis.

Statistical Analysis

The results are expressed as mean values±standard deviation of the mean (±S.E.M.). The statistical significance of differences between groups was evaluated by Student's t-test. $p \leq 0.05$ was accepted as statistically significant. All statistical calculations were performed using the computer software described by Tallarida and Murray.

Results

Morphine

The study shows that a single administration of a micronized or normal form of magnesium lactate or magnesium chloride at a dose of 15 mg magnesium ions/kg body mass (p.o.) with morphine at a dose of 15 mg/kg body mass (p.o.) significantly enhanced morphine analgesia. The activity of micronized magnesium lactate was not only marked but also appeared earlier (already 30 minutes into the study) and lasted up to 240 min as compared to normal magnesium (from 60 to 180 min). The activity of magnesium chloride both in micronized form and in normal form on morphine analgesia was similar to the activity of the micronized form of magnesium lactate.

Neither morphine nor magnesium lactate and chloride in micronized or normal form administered alone showed analgesic activity.

Figure 2:
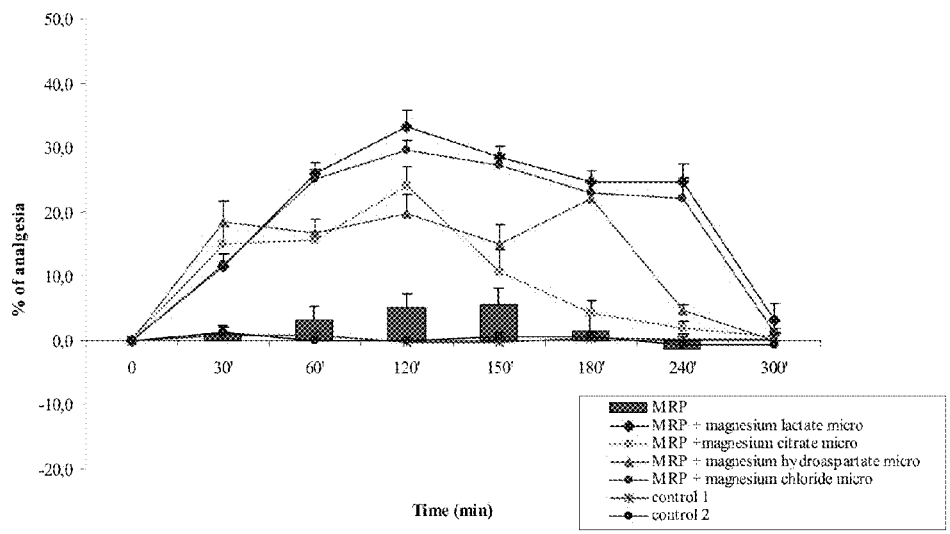
FIG. 2 represents the influence of magnesium salts at a dose of 15 mg magnesium ions/kg body mass (p.o.) on morphine analgesia (MRP, 15 mg/kg body mass, p.o.). Wherein in the combined graph: control 1—0.5% methylcellulose solution, control 2—distilled water.

The administration of equivalent doses of micronized magnesium hydroaspartate and citrate (15 mg of magnesium ions/kg body mass, p.o.) concomitantly with morphine (15 mg/kg body mass, p.o.) also enhanced morphine analgesia. This activity was weaker, although significant, and lasted for a shorter time (magnesium citrate up to 120 min; magnesium hydroaspartate up to 180 min) than in the case of micronized form of magnesium lactate. The activity of these same magnesium salts on morphine analgesia was much weaker only in normal form, as compared to the micronized form. Both magnesium citrate and hydroaspartate administered alone in micronized or normal form did not alter the pain threshold (FIG. 1A, B, C, D; FIG. 2).

A 7-day premedication with micronized magnesium lactate (15 mg magnesium ions/kg p.o., also enhanced the analgesic activity of morphine (15 mg/kg body mass, p.o.). This activity began on day 3 of the measurement, grew gradually to 7 day. Cessation of drug administration resulted in gradual return to baseline values. The activity of normal magnesium lactate on morphine analgesia (at a 2× larger dose of 30 mg magnesium ions/kg body mass, p.o.) was much weaker and appeared only on days 6 and 7 of the measurements (FIG. 3). The separate administration of morphine slightly increased the threshold for mechanical nociceptive stimuli, whereas the separate administration of magnesium lactate in micronized form or normal form did not alter the pain threshold (FIG. 3).

Codeine

A single administration of a micronized or normal form of magnesium lactate or magnesium chloride at a dose of 15 mg magnesium ions/kg body mass (p.o.) with codeine at a dose of 175 mg/kg body mass (p.o.) significantly enhanced the analgesic activity of codeine. The activity of micronized magnesium salts was particularly strong in min 45 of the study.

The administration of equivalent doses of micronized magnesium hydroaspartate or citrate (15 mg magnesium ions/kg body mass, p.o.) with codeine (175 mg/kg body mass, p.o.) also enhanced codeine analgesia. The activity of the same magnesium compounds in normal form on codeine analgesia was significantly weaker (FIG. 4 A, B, C, D; FIG. 5). The separate administration of codeine and the micronized, as well as the normal, form of lactate, chloride, hydroaspartate and citrate of magnesium did not exhibit analgesic activity (FIG. 4).

A 7-day administration of micronized magnesium lactate (15 mg magnesium ions/kg body mass, p.o.) also enhanced analgesic activity of chronically administered codeine (175 mg/kg body mass, p.o.). The activity began on the fourth day of measurement, reached a maximum on days 6 and 7, and then after cessation of drug administration rapidly decreased. The activity of normal magnesium lactate (at a dose of 30 mg magnesium ions/kg body mass, p.o.) was significantly weaker and only appeared on days 6 and 7 of the measurements (FIG. 6).

Separately administered codeine as well as the micronized or normal form magnesium lactate did not exhibit analgesic activity (FIG. 6).

Tramadol

A single administration of the micronized or normal form magnesium lactate and magnesium chloride (in both forms) at a dose of 15 mg magnesium ions/kg p.o., increased antynociceptive activity of tramadol (125 mg/kg body mass, p.o.). The enhancement of opioid analgesia by magnesium appeared in min 5, with maximum activity at min 15 and lasted until min 45 (for magnesium lactate) or min 90 (for magnesium chloride) following the administration of the opioid. Activity of the normal form of magnesium lactate as opposed to the normal form of magnesium chloride on tramodol analgesia was weaker than the micronized form.

The administration of equivalent doses of magnesium hydroaspartate and citrate in micronized forms (15 mg magnesium ions/kg body mass, p.o.) concomitantly with tramadol (125 mg/kg body mass, p.o.) also enhanced tramadol analgesia. The activity of micronized magnesium citrate was similar to the activity of the magnesium chloride, whereas the activity of micronized magnesium hydroaspartate was weaker throughout the study.

The same magnesium salts given in normal form enhanced tramadol analgesia less in comparison to the micronized form (FIG. 7A, B, C, D; FIG. 8).

The separate administration of tramadol as well as the micronized and normal form of lactate, chloride, aspartate and magnesium citrate did not exhibit analgesic activity (FIG. 7).

Micronized magnesium lactate (15 mg magnesium ions/kg body mass, p.o.) administered for 10 consecutive days with tramadol (125 mg/kg body mass, p.o.) enhanced the long-term analgesic activity of the examined opioid. The activity began on the third day, gradually increased (to day 7), and then was maintained to day 10 of the measurements. After the removal of the tested substances, the pain threshold returned to control values by day 11 of the measurements. The activity of normal magnesium lactate (at a dose of 30 mg magnesium ions/kg body mass, p.o.) was similar to the micronized form up to day 6 of the measurements and then significantly weaker (FIG. 9).

The separate administration of tramadol insignificantly intensified the threshold for mechanical nociceptive stimuli from days 6 to 10 of the measurements, whereas the separate administration of magnesium lactate in micronized form or normal form did not alter the pain threshold (FIG. 9).

Oxycodone

A single administration of the micronized or normal form of magnesium lactate or magnesium chloride at a dose of 15 mg magnesium ions/kg body mass (p.o.) significantly enhanced oxycodone analgesia (5 mg/kg body mass, p.o.). The activity appeared already in the min 5, and in the case of the micronized form was maintained at a constant level up to min 30 of the study, then became weaker in min 45 and disappeared in min 60. The activity of the normal form of magnesium lactate on oxycodone analgesia was weakened by min 15 and 30 and was maintained up to min 45 following the administration of the opioid. The activity of the normal form of magnesium chloride was similar to the activity of the micronized form of this salt.

The administration of equivalent doses of magnesium hydroaspartate or citrate (15 mg magnesium ions/kg body mass, p.o.) with oxycodone (5 mg/kg body mass, p.o.) also enhanced oxycodone analgesia. The same magnesium salts administered in normal form enhanced oxycodone analgesia significantly less when compared to the micronized form (FIG. 10 A, B, C, D; FIG. 11).

The separate administration of oxycodone or the micronized, as well as the normal, forms of magnesium lactate, chloride, hydroaspartate and citrate showed no analgesic activity (FIG. 10).

The form of magnesium lactate (15 mg magnesium ions/kg body mass, p.o.) administered for 7 consecutive days together with oxycodone (5 mg/kg body mass, p.o.) enhanced the long-term analgesic activity of the examined opioid. The activity began on the third day of measurement and reached its maximum on days 6 and 7 of the study. One day after the removal of the tested substances, we observed a rapid return of the pain threshold to control values. The activity of normal magnesium lactate (at a dose 2× larger—30 mg magnesium ions/kg body mass, p.o.) was similar in the initial phase of the treatment (to day 5) where after it became weaker compared to the micronized form (FIG. 12).

Separate administration of oxycodone as well as magnesium lactate in micronized form or normal form did not exhibit analgesic activity (FIG. 12).

Dihydrocodeine

A single administration of the micronized or normal form of magnesium lactate and also magnesium chloride in both forms at a dose of 15 mg magnesium ions/kg body mass, p.o.) together with dihydrocodeine at a dose of 50 mg/kg body mass (p.o.) significantly enhanced dihydrocodeine analgesia. The activity gradually increased and reached a maximum between min 45 and 90 of the measurements and then became weaker by min 210 of the measurements.

The activity of the normal form of magnesium (chloride or lactate) also enhanced dihydrocodeine analgesia, but compared to micronized magnesium this was somewhat weaker.

The administration of equivalent doses of micronized hydroaspartate or magnesium citrate (15 mg magnesium ions/kg body mass, p.o.) with dihydrocodeine (50 mg/kg body mass, p.o.) also enhanced dihydrocodeine analgesia, though the activity compared to magnesium lactate lasted a shorter time. The activity of the same magnesium compound in normal form was significantly weaker (FIG. 13 A, B, C, D; FIG. 14).

The separate administration of dihydrocodeine only insignificantly raised the pain perception threshold (90-120 min) whereas the separate administration of micronized or normal forms of lactate, chloride, hydroaspartate and magnesium citrate did not exhibit analgesic activity (FIG. 13).

A 7-day administration of micronized magnesium lactate (15 mg magnesium ions/kg body mass, p.o.) gradually enhanced the analgesic activity of chronically administered dihydrocodeine (50 mg/kg body mass, p.o.). The activity began on the fourth day of measurement, reached a maximum on days 6 and 7 of the study and then after cessation of drug administration the pain threshold rapidly reduced to control values. The activity of ordinary magnesium lactate (at a 2× greater dose of 30 mg magnesium ions/kg body mass, p.o.) was significantly weaker in comparison to the micronized form.

The separate administration of dihydrocodeine insignificantly raised the nociceptive stimulus threshold on days 6 and 7 of the measurements, whereas the separate administration of magnesium lactate in micronized form or normal form did not alter the pain threshold (FIG. 15).

Effect of Magnesium Salts on Opioid-Induced Constipations

It was observed that the oral administration of salts of magnesium, both in micronized and in normal form, seemed to decrease opioid-related bowel obstruction. Fecal pellets following the administration of the same opioids were very dry, whereas the co-administration of the opioid with magnesium salts resulted in increased fecal pellet moisture content. The fecal pellets were more similar to normal ones.

Summary

Magnesium compounds, particularly salts, regardless of form (micronized or normal) increase the analgesic activity of opioids administered orally. However, in the case of micronized magnesium salts, additional intensification of the opioid analgesia occurred. The effect seems to be caused by accelerated absorption of micronized magnesium salt uptake in the gastrointestinal tract.

The invention claimed is:

1. An analgesic pharmaceutical composition for oral administration, comprising an opioid and a pharmaceutically admissible salt of magnesium (II) selected from the group consisting of magnesium lactate, magnesium hydroaspartate, and magnesium citrate, wherein said salt of magnesium (II) is in a particulated form of D90<200 μm in size, and optionally further comprising one or more pharmaceutically admissible ancillary substances.

2. The composition according to claim 1, wherein the opioid is a phenanthrene derivative of opium.

3. The composition of claim 1, wherein the opioid is tramadol.

4. The composition of claim 1, wherein the salt of magnesium (II) is in a particulated form of D90<50 μm in size.

5. The composition of claim 2, wherein said opioid is selected from the group consisting of morphine, codeine, dihydrocodeine, and oxycodone.

6. A method for treating pain in a patient in need thereof, said method comprising administering the composition of claim 1 orally to said patient.

7. The method according to claim 6, wherein the opioid is a phenanthrene derivative of opium.

8. The method according to claim 6, wherein the opioid is tramadol.

9. The method of claim 7, wherein the opioid is selected from the group consisting of morphine, codeine, dihydrocodeine, and oxycodone.

10. The method of claim 6, wherein the salt of magnesium (II) is in a particulated form of D90<50 μm in size.

* * * * *